United States Patent [19]
Fuchs et al.

[11] 3,973,947
[45] Aug. 10, 1976

[54] 1,3,5-TRIAZINEDIONES AND THEIR USE AS SELECTIVE HERBICIDES

[75] Inventors: Julius Jakob Fuchs, Wilmington; Kang Lin, Newark, both of Del.

[73] Assignee: E. I. Du Pont de Nemours and Company, Wilmington, Del.

[22] Filed: Aug. 20, 1974

[21] Appl. No.: 499,045

Related U.S. Application Data

[60] Division of Ser. No. 301,853, Oct. 30, 1972, Pat. No. 3,855,219, which is a continuation-in-part of Ser. No. 268,767, July 3, 1972, abandoned, which is a continuation-in-part of Ser. No. 181,202, Sept. 16, 1971, abandoned.

[52] U.S. Cl. .................................................. 71/93
[51] Int. Cl.$^2$ ...................... A01N 9/22; A01N 9/12
[58] Field of Search .......................................... 71/93

[56] References Cited
UNITED STATES PATENTS 3,040,044  6/1962  Hirsch et al. ......................... 71/93 X
3,544,570  12/1970  Timmler et al. ...................... 71/93 X Primary Examiner—Lewis Gotts
Assistant Examiner—Catherine L. Mills

[57] ABSTRACT 1,3,5-Triazinediones of the formula

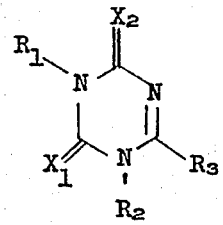

wherein $X_1$, $X_2$, $R_1$, $R_2$ and $R_3$ are as hereinafter defined, are useful for the selective control of weeds in crops, e.g., corn. Many are also useful for altering plant flowering and plant sexual reproduction.

Exemplary of the class of compounds are 3-isopropyl-6-methylthio-s-triazine-2,4(1H,3H)-dione, 3-(p-chlorophenyl)-6-methoxy-s-triazine-2,4(1H,3H)-dione.

3 Claims, No Drawings

1,3,5-TRIAZINEDIONES AND THEIR USE AS SELECTIVE HERBICIDES

CROSS REFERENCE TO RELATED APPLICATIONS

This application is a division of application Ser. No. 301,853, filed Oct. 30, 1972, now U.S. Pat. NO. 3.855,219, granted Dec. 17, 1974, which is a continuation-in-part of application Ser. No. 268,767, filed July 3, 1972, now abandoned, which is, in turn, a continuation-in-part of application Ser. No. 181,202, filed Sept. 16, 1971, now abandoned.

BACKGROUND OF THE INVENTION

This invention relates to s-triazine herbicides.

Neumayer et al., "Pesticides", Chemical Week, Apr. 12 and 26, 1969, lists several commercial and experimental s-triazine herbicides. Among these are prometone and prometryne, which have the structural formulae:

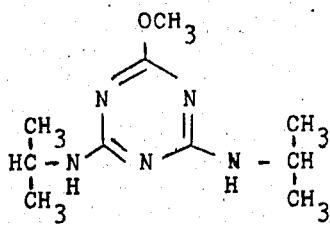

prometone

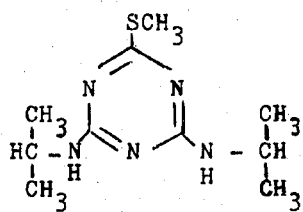

prometryne

These and related compounds are disclosed in U.S. Pat. No. 2,909,420.

SUMMARY OF THE INVENTION

It has now been discovered that compounds of formula I are useful as selective herbicides for controlling broadleaf and grass weeds in such crops as rice, asparagus and corn. Many of the compounds are also useful, at lower rates of application, for altering plant flowering and plant sexual reproduction.

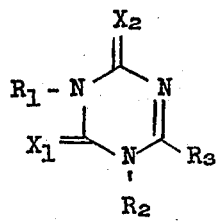

I wherein
$R_1$ is alkyl of 1 through 8 carbon atoms, cycloalkyl of 3 through 8 carbon atoms, cycloalkyl of 4 through 7 carbon atoms, alkenyl of 3 through 4 carbon atoms, alkynyl of 3 through 4 carbon atoms, benzyl or

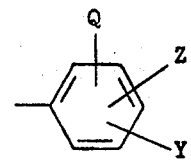

where
Y is hydrogen, halogen, alkyl of 1 through 4 carbon atoms, nitro, alkoxy of 1 through 4 carbon atoms, alkylthio of 1 through 4 carbon atoms, cyano or trifluoromethyl,
Z is hydrogen, halogen, methyl, ethyl, nitro, alkoxy of 1 through 4 carbon atoms, or alkylthio of 1 through 4 carbon atoms, and
Q is hydrogen, halogen, or methyl;
$R_2$ is hydrogen, a group

where A is alkyl of 1 through 3 carbon atoms or alkoxy or alkylthio of 1 through 4 carbon atoms, or a cation selected from lithium, sodium, potassium, calcium, magnesium, barium, or

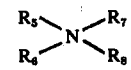

where $R_5$, $R_6$ and $R_7$ can be the same or different and each can be hydrogen, alkyl of 1 through 4 carbon atoms, or hydroxy alkyl of 2 through 4 carbon atoms; and $R_8$ is hydrogen, alkyl of 1 through 12 carbon atoms, or benzyl; $R_5$ and $R_6$ can be taken together to form a ring that is $-(CH_2)_2-O-(CH_2)_2-$ or $-(CH_2)_n-$ where $n$ is 4-6 and $R_7$ and $R_8$ are H;
$R_3$ is $SR_4$ or $OR_4$,
where
$R_4$ is alkyl of 1 through 6 carbon atoms, cycloalkyl of 3 through 6 carbon atoms, alkenyl of 3 through 4 carbon atoms, alkynyl of 3 through 4 carbon atoms, or benzyl, and
$X_1$ and $X_2$ are oxygen or sulfur.

Preferred within the above formula because of ease of synthesis and higher herbicidal activity are the compounds where:
$R_1$ is alkyl of 3 through 6 carbon atoms or alkenyl of 3 through 4 carbon atoms;
$R_2$ is hydrogen;
$R_3$ is $SR_4$ or $OR_4$;
$R_4$ is alkyl of 1 through 6 carbon atoms or alkenyl of 3 through 4 carbon atoms; and
$X_1$ and $X_2$ are oxygen.

More preferred because of their highest herbicidal activity are those compounds of the formula where:
$R_1$ is alkyl of 3 through 4 carbon atoms;
$R_2$ is hydrogen;
$R_3$ is $SCH_3$, $SC_2H_5$, $OCH_3$ or $OC_2H_5$; and $X_1$ and $X_2$ are oxygen.

Preferred herbicidal compounds within the above formula include:

3-tert-butyl-6-methylthio-s-triazine-2,4(1H,3H)-dione
3-sec-butyl-6-methylthio-s-triazine-2,4(1H,3H)-dione
3-isopropyl-6-methylthio-s-triazine-2,4(1H,3H)-dione
3-isopropyl-6-methoxy-s-triazine-2,4(1H,3H)-dione
3-isopropyl-6-ethoxy-s-triazine-2,4(1H,3H)-dione Preferred for altering plant flowering and/or plant sexual reproduction are those compounds of Formula I, $R_4$ is methyl or ethyl, Y is hydrogen, halogen or methyl, Z is halogen, and Q is hydrogen.

Most preferred for altering plant flowering and/or plant sexual reproduction are:
1. 3-(4-chlorophenyl)-6-methylthio-s-triazine-2,4(1H,3H)-dione
2. 3-(4-chlorophenyl)-6-methoxy-s-triazine-2,4(1H,3H)-dione
3. 3-(4-bromophenyl)-6-methoxy-s-triazine-2,4(1H,3H)-dione
4. 3-(3,4-difluorophenyl)-6-methoxy-s-triazine-2,4(1H,3H)-dione
5. 3-(4-methylphenyl)-6-methoxy-s-triazine-2,4(1H,3H)-dione
6. 3-(2-chlorophenyl)-6-methoxy-s-triazine-2,4(1H,3H)-dione
7. 3-(4-fluorophenyl)-6-methoxy-s-triazine-2,4(1H,3H)-dione
8. 3-(2,4-dichlorophenyl)-6-methoxy-s-triazine-2,4(1H,3H)-dione
9. 3-(2-methylphenyl)-6-methoxy-s-triazine-2,4(1H,3H)-dione.

DETAILED DESCRIPTION OF THE INVENTION wherein $R_1$, $R_3$, $X_1$ and $X_2$ are as previously defined.

The synthesis of allophanimidates and 3-thioallophanimidates from pseudourea and the synthesis of 1-thioallophanimidates and 1,3-dithioallophanimidates from thiopseudourea (Equation 1) can be performed analogous to a procedure given in Organic Synthesis 42, 84, which describes the preparation of methyl 4-phenyl-3-thioallophanimidate (1-phenyl-2-thio-4-methylisobiuret).

The reaction products of Equation (1) are reacted at about 0°–45°C in a solvent, e.g. methylene chloride, with one equivalent of a chloroformate or a chlorothiolformate in the presence of one equivalent of a base such as triethylamine (Equations 2a and 2b). After completion of the reaction, the methylene chloride solution is washed with water, dried, and the solvent evaporated to give alkoxycarbonylallophanimidates, alkylthiolcarbonylallophanimidates, alkoxycarbonylthioallophanimidates, alkylthiolcarbonylthioallophanimidates, alkoxycarbonyldithioallophanimidates and alkylthiolcarbonyldithioallophanimidates. Using a chlorodithioformate in the above reaction affords the corresponding alkylthiolthiocarbonylallophanimidates, alkylthiolthiocarbonylthioallophanimidates and alkylthiolthiocarbonyldithioallophanimidates.

The reaction product of Equation (2a) and Equation (2b) are then refluxed for a sufficient time with a base such as sodium methoxide in methanol to effect cyclization (Equations 3a and 3b). The solvent is then evaporated under vacuum and the residue dissolved in water. Acidification of the aqueous solution usually precipitates the desired s-triazinediones, thio-s-triazinediones or s-triazinedithiones as a substantially pure solid.

The reaction product of Equations (2a) and (2b) are also obtained by reacting the pseudourea or thiopseudourea first with a chloroformate, a chlorothiolfor-

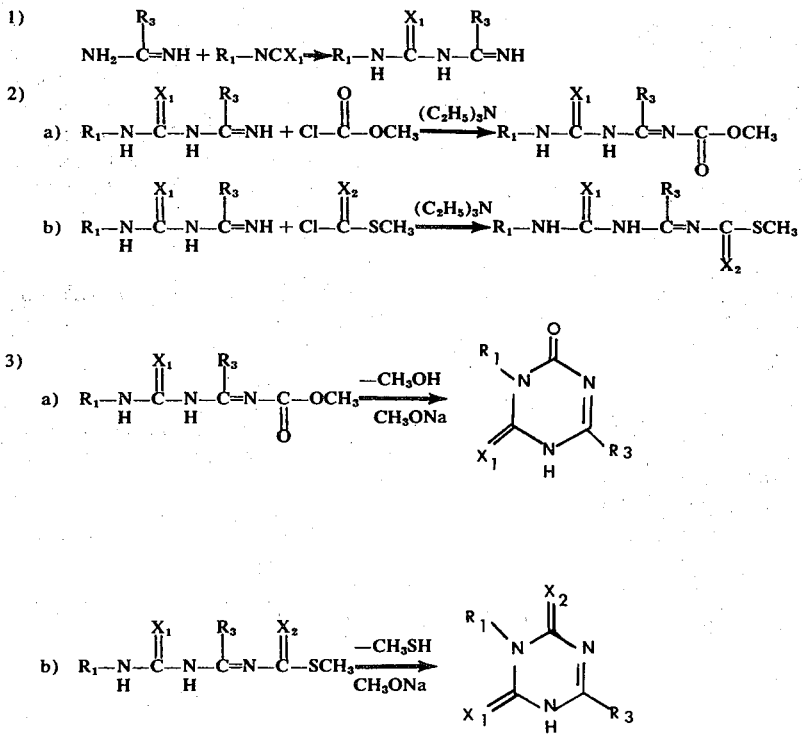

mate or a chlorodithioformate as in Equations (4a) and (4b), and then reacting the reaction products of Equations (4a) and (4b) with an isocyanate or isothiocyanate as in Equations (5a) and (5b).

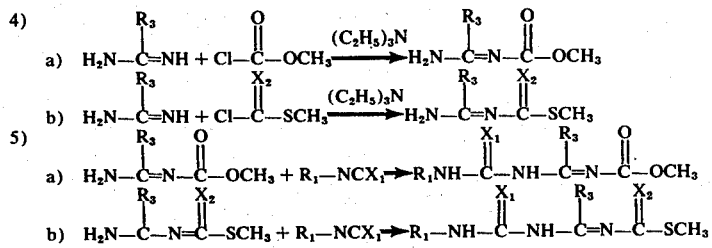

wherein $R_1$, $R_3$, $X_1$ and $X_2$ are as previously defined.

Reacting the intermediate allophanimidates of equation (1) with phosgene or thiophosgene at temperatures of 0° to 100°C also gives the s-triazinediones of this invention:

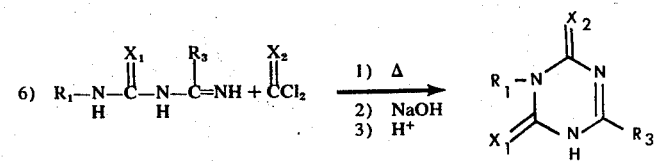

where A is an alkyl, alkylthio or alkoxy group.

The s-triazinediones form salts which are useful alone or can be reacted with an acyl chloride, an alkyl chloroformate, or an alkyl chlorothiolformate to give 1-substituted analogs as illustrated by the following equations:

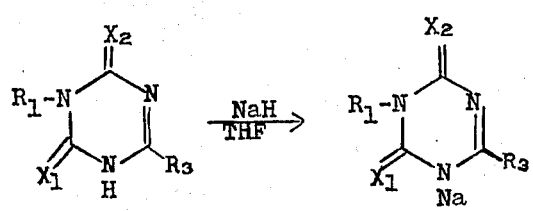

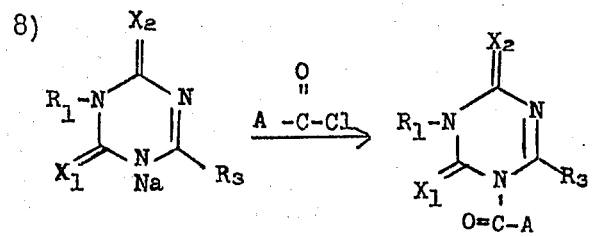

The following examples are offered to illustrate the processes described above. All parts are parts by weight unless otherwise indicated.

EXAMPLE 1

3-tert-Butyl-6-methylthio-s-triazine-2,4(1H,3H)-dione

To a solution of 139 parts of 2-methyl-2-thiopseudourea sulfate in 1000 parts of 50% aqueous methanol at 0°C is added dropwise 88 parts of 50% sodium hydroxide, followed by 90 parts tert-butyl isocyanate in 200 parts tetrahydrofuran. The solution is concentrated at reduced pressure and filtered to yield, after drying, 90 parts of methyl 4-tert-butyl-1-thioallophanimidate melting at 102°–104°C.

To a solution of 5.67 parts of the above compound and 4 parts of triethylamine in 50 parts methylene chloride at 0°C is added dropwise 3.3 parts methyl chlorothiolformate in 5 parts of methylene chloride. The solution is stirred overnight and washed once with water. After drying and evaporation of the solvent, there is obtained 3.8 parts methyl 4-tert-butyl-N-methylthiolcarbonyl-1-thioallophanimidate melting at 102°–105°C.

A solution of five parts of the above compound in 50 parts of methanol containing 3 parts of sodium methoxide is refluxed for 1 hour. The reaction mixture is then cooled and the methanol is evaporated at reduced pressure. One hundred parts of water are added and the solution twice extracted with 50 parts of ether. The aqueous layer is then neutralized at 0° to 5°C. with hydrochloric acid and extracted with methylene chloride. The methylene chloride extract is dried and the solvent evaporated to give 3 parts of 3-tert-butyl-6-methylthio-s-triazine-2,4(1H,3H)-dione, melting at 112°–115°C.

EXAMPLE 2

3-Isopropyl-6-methylthio-s-triazine-2,4(1H,3H)-dione

To a solution of 69.5 parts of 2-methyl-2-thiopseudourea sulfate and 47 parts of methyl chloroformate in 1000 parts of water at 0°C is added dropwise 56.9 parts of potassium hydroxide in 200 parts of water. The reaction mixture is stirred at room temperature for 3 hours and then extracted with methylene chloride. The methylene chloride extract is dried and the solvent evaporated at reduced pressure to give 45 g of methyl N-(1-amino-1-methylthiomethylene)carbamate melting at 72°–77°C.

A solution of seventy-four parts of the above compound and 47 parts of isopropyl isocyanate in 300 parts methylene chloride is stirred overnight. The solvent is evaporated to give 113.6 parts of methyl 4-isopropyl-N-methoxycarbonyl-1-thioallophanimidate melting at 129°–132°C.

A solution of one hundred parts of the above compound in 200 parts of methanol containing 27 parts of sodium methoxide is refluxed for one hour. The methanol is evaporated under vacuum and the residue dissolved in 200 parts of water. The aqueous solution is neutralized with hydrochloric acid to afford after filtration and drying 55 parts of 3-isopropyl-6-methylthio-s-triazine-2,4(1H,3H)-dione melting at 188°–190°C.

EXAMPLE 3

3-Methyl-6-methylthio-s-triazine-2,4(1H,3H)-dione

To a solution of 69.5 parts of 2-methyl-2-thiopseudourea sulfate and 110 parts of methyl chlorothiolformate in 500 ml of water is added dropwise at 0°–5°C 120 parts of 50% sodium hydroxide. The reaction mixture is stirred at 0°–5°C for 1 hour and then at room temperature for 2 hours. The solution is then extracted with methylene chloride and the organic extract dried and evaporated under vacuum to give 47 parts of methyl N-(1-amino-1-methylthiomethylene)-thiolcarbamate melting at 75°–76°C.

To a solution of 8.2 parts of the above compound in 75 parts of methylene chloride is added 3.1 parts of methyl isocyanate. The reaction mixture is stirred at room temperature for 3 hours, and then the solvent evaporated under vacuum to give 10 parts of methyl 4-methyl-N-methylthiolcarbonyl-1-thiolallophanimidate melting at 115°–117°C.

A solution of six parts of the above compound in 75 parts of methanol containing 4.5 parts sodium methoxide is refluxed for 1 hour. The methanol is evaporated and the residue dissolved in water. The aqueous solution is then neutralized with hydrochloric acid at 0°–5°C. The precipitate is collected by filtration and dried to give 2.3 parts of 3-methyl-6-methylthio-s-triazine-2,4(1H,3H)-dione melting at 243°–244°C.

EXAMPLE 4

3-(p-Chlorophenyl)-6-methylthio-s-triazine-2,4-(1H,3H)-dione

To a solution of 148 parts of methyl N-(1-amino-1-methylthiomethylene)-carbamate, prepared as in Example 2, in 2,000 parts methylene chloride is added 154 parts of p-chlorophenyl isocyanate. The reaction is stirred for 3 days. Then to it is added 54 parts of sodium methoxide in 540 parts of methanol. Th reaction mixture is then refluxed for 1 hour. The reaction mass is cooled, and 2,000 parts of ether are added. The solid collected by filtration is dissolved in water and the solution neutralized with hydrochloric acid. The new solid thus formed is collected, dried, and recrystallized from ethanol/H$_2$O to give 140 parts of 3-(p-chlorophenyl)-6-methylthio-s-triazine-2,4(1H,3H)-dione melting at 292°–295°C.

EXAMPLE 5

3-sec-Butyl-6-methylthio-s-triazine-2,4(1H,3H)-dione

To a solution of 7.2 parts of methyl N-(1-amino-1-methylthiomethylene)carbamate, prepared as in Example 2, in 50 parts of methylene chloride is added 5.5 parts of sec-butyl isocyanate. The reaction mixture is stirred overnight and the solvent evaporated to give 12 parts of crude methyl 4-sec-butyl-N-methoxycarbonyl-1-thioallophanimidate melting at 102°–104°C.

The above product is refluxed for 1 hour in 150 parts of methanol containing 6 parts of sodium methoxide. The solvent is evaporated under vacuum and the residue is dissolved in 100 parts of water. The aqueous solution is extracted with methylene chloride and the aqueous layer then neutralized at 0°–5°C with hydrochloric acid. The aqueous solution is extracted again with methylene chloride. The extract is dried and the methylene chloride evaporated to give 7 parts of a solid melting at 124°–132°C. Recrystallization from chlorobutane gives 4 parts of 3-sec-butyl-6-methylthio-s-triazine-2,4(1H,3H)-dione, melting at 133.5°–135.5°C.

EXAMPLE 6

3-(p-Chlorophenyl)-6-methoxy-s-triazine-2,4(1H,3H)-dione

To 52 parts of 2-methylpseudourea hydrogen sulfate in 250 parts of water at 0°–5°C is added 31 parts of methyl chloroformate followed by dropwise addition of 74 parts of 50% sodium hydroxide. The reaction mass is stirred at room temperature for 3 hours and then extracted with methylene chloride. The methylene chloride extract is dried and the solvent evaporated. The residue is triturated with hexane to give 23 parts of methy N-(1-amino-1-methoxy-methylene)-carbamate melting at 36°–39.5°C.

To 13 parts of the compound prepared above in 200 ml of methylene chloride is added 15 parts of p-chorophenyl isocyanate. The reaction mass is stirred overnight. The solvent is evaporated and the residue refluxed overnight in 100 parts of 10% sodium methoxide in methanol. Water is added and the solution neutralized with hydrochloric acid. The crude solid collected by filtration is recrystallized from acetonitrile to give 7 parts of 3-(p-chlorophenyl)-6-methoxy-s-triazine-2,4(1H,3H)-dione melting at 238°–241°C.

EXAMPLE 7

3-(2-Methyl-4-chlorophenyl)-6-methoxy-s-triazine-2,4(1H,3H)-dione

To 20 parts of methyl N-(1-amino-1-methoxymethylene)carbonate prepared as in Example 6 in 200 parts of methylene chloride is added 25 parts of 2-methyl-4-chlorophenyl isocyanate. It is stirred overnight and 8 parts sodium methoxide in 80 parts of methanol is added. It is refluxed for 1 hour and the solid is collected by filtration. It is dissolved in water and the solution neutralized at 0°–5°C. with concentrated hydrochloric acid. The precipitate is collected by filtration to give 25 parts of 3-(2-methyl-4-chlorophenyl)-6-methoxy-s-triazine-2,4(1H,3H)-dione melting at 193°–195°C.

EXAMPLE 8

3-(o-fluorophenyl)-6-methylthio-s-triazine-2,4(1H,3H)-dione

To a solution of 16 parts of methyl N-(1-amino-1-methylthiomethylene)carbamate, prepared as in Example 2, in 150 parts of methylene chloride is added 15 parts of o-fluorophenyl isocyanate. The reaction mixture is stirred overnight and the solvent evaporated to give after trituration with hexane 29 parts of methyl 4-(o-fluorophenyl)-N-methoxycarbonyl-1-thioallophanimidate melting at 123°–125°C.

Sixteen parts of the above product are refluxed for 1 hour in 150 parts of methanol containing 9 parts of sodium methoxide. The solvent is evaporated under vacuum and the residue is dissolved in 200 parts of water. The aqueous solution is extracted with methylene chloride and the aqueous layer then neutralized at 0°–5°C. with hydrochloric acid. The precipitate is collected and dried to give 11 parts of 3-(o-fluorophenyl)-6-methylthio-s-triazine-2,4(1H,3H)-dione melting at 196°–199°C.

EXAMPLE 9

The following s-triazinediones can be prepared by the procedure of Example 2 by substituting the listed 2-substituted thiopseudoureas and pseudoureas, for 2-methyl-2-thiopseudourea, by using various chloroformates and by replacing isopropyl isocyanate with various isocyanates or isothiocyanates.

| Thiopseudourea or Pseudourea | Isocyanate or Isothiocyanate | Formates | s-Triazinediones |
|---|---|---|---|
| 2-methyl-2-thiopseudourea | ethyl isocyanate | methyl chloroformate | 3-ethyl-6-methylthio-triazine-2,4-(1H,3H)-dione, m.p. 190–191° |
| " | phenyl isocyanate | " | 3-phenyl-6-methylthio-s-triazine-2,4-(1H,3H)-dione, m.p. 235–245° |
| " | cyclohexyl isocyanate | " | 3-cyclohexyl-6-methylthio-s-triazine-2,4(1H,3H)-dione, m.p. 255–257° |
| " | o-fluorophenyl isocyanate | " | 3-(o-fluorophenyl)-6-methylthio-s-triazine-2,4(1H,3H)-dione, m.p. 196–199° |
| " | o-nitrophenyl isocyanate | " | 3-(o-nitrophenyl)-6-methylthio-s-triazine-2,4(1H,3H)-dione, m.p. 196–202° |
| " | propyl isocyanate | " | 3-propyl-6-methylthio-s-triazine-2,4-(1H,3H)-dione, m.p. 145–148° |
| " | m-tolyl isocyanate | " | 3-(m-tolyl)-6-methylthio-s-triazine-2,4-(1H,3H)-dione, m.p. 176–180° |
| " | allyl isocyanate | " | 3-allyl-6-methylthio-s-triazine-2,4(1H,3H)-dione, m.p. 140–142° |
| " | 3,4-dichlorophenyl isocyanate | " | 3-(3,4-dichlorophenyl)-6-methylthio-s-triazine-2,4(1H,3H)-dione, m.p. 269–271° |
| " | p-fluorophenyl isocyanate | " | 3-(p-fluorophenyl)-6-methylthio-s-triazine-2,4(1H,3H)-dione, m.p. 239–243° |
| " | p-nitrophenyl isocyanate | " | 3-(p-nitrophenyl)-6-methylthio-s-triazine-2,4(1H,3H)-dione, m.p. 279–280.5° |
| " | p-bromophenyl isocyanate | " | 3-(p-bromophenyl)-6-methylthio-s-triazine-2,4(1H,3H)-dione, m.p. 272–273° |
| " | o-chlorophenyl isocyanate | " | 3-(o-chlorophenyl)-6-methylthio-s-triazine-2,4(1H,3H)-dione, m.p. 212.5–214° |
| " | m-chlorophenyl isocyanate | " | 3-(m-chlorophenyl)-6-methylthio-s-triazine-2,4(1H,3H)-dione, m.p. 192–195.5° |
| " | cyclohexylmethyl isocyanate | " | 3-cyclohexylmethyl-6-methylthio-s-triazine-2,4(1H,3H)-dione, m.p. 177.5–178° |
| 2-allyl-2-thiopseudourea | isopropyl isocyanate | " | 3-isopropyl-6-allylthio-s-triazine-2,4-(1H,3H)-dione, m.p. 140–142° |
| 2-methylpseudourea | phenyl isocyanate | " | 3-phenyl-6-methoxy-s-triazine-2,4(1H,3H)-dione, m.p. 198–200° |
| " | cyclohexyl isocyanate | " | 3-cyclohexyl-6-methoxy-s-triazine-2,4-(1H,3H)-dione, m.p. 212–220° |
| " | p-fluorophenyl isocyanate | " | 3-(p-fluorophenyl)-6-methoxy-s-triazine-2,4(1H,3H)-dione, m.p. 234–237° |
| " | m-chlorophenyl isocyanate | " | 3-(m-chlorophenyl)-6-methoxy-s-triazine-2,4(1H,3H)-dione, m.p. 183–185.5° |
| " | m-fluorophenyl isocyanate | " | 3-(m-fluorophenyl)-6-methoxy-s-triazine-2,4(1H,3H)-dione, m.p. 184–186° |
| " | sec-butyl isocyanate | " | 3-sec-butyl-6-methoxy-s-triazine-2,4(1H,3H)-dione, m.p. 121–122.5° |
| 2-ethylpseudourea | p-chlorophenyl isocyanate | " | 3-(p-chlorophenyl)-6-ethoxy-s-triazine-2,4-(1H,3H)-dione, m.p. 241–242° |
| 2-methylpseudourea | p-nitrophenyl isocyanate | " | 3-(p-nitrophenyl)-6-methoxy-s-triazine-2,4-(1H,3H)-dione, m.p. 290–292° |
| " | p-bromophenyl isocyanate | " | 3-(p-bromophenyl)-6-methoxy-s-triazine-2,4-(1H,3H)-dione, m.p. 208–210° |
| " | 3,4-dichlorophenyl isocyanate | " | 3-(3,4-dichlorophenyl)-6-methoxy-s-triazine-2,4(1H,3H)-dione, m.p. 197–199° |
| 2-methyl-2-thiopseudourea | phenyl isothiocyanate | " | 3-phenyl-6-methylthio-2-thio-s-triazine-2,4(1H,3H)-dione, m.p. 235–238° |
| 2-methylpseudourea | p-methoxyphenyl isocyanate | " | 3-(p-methoxyphenyl)-6-methoxy-s-triazine-2,4(1H,3H)-dione, m.p. 213–214° |
| " | p-tolyl isocyanate | " | 3-(p-tolyl)-6-methoxy-s-triazine-2,4-(1H,3H)-dione, m.p. 225–226° |
| " | benzyl isocyanate | " | 3-benzyl-6-methoxy-s-triazine-2,4(1H,3H)-dione, m.p. 169–170° |
| 2-hexyl-2-thiopseudourea | propyl isocyanate | " | 3-propyl-6-hexylthio-s-triazine-2,4-(1H,3H)-dione |
| 2-cyclopropyl-2-thiopseudourea | cyclopropyl isocyanate | " | 3-cyclopropyl-6-cyclopropylthio-s-triazine-2,4(1H,3H)-dione |

-continued

| Thiopseudourea or Pseudourea | Isocyanate or Isothiocyanate | Formates | s-Triazinediones |
|---|---|---|---|
| 2-cyclohexyl-2-thiopseudourea | cyclooctyl isocyanate | " | 3-cyclooctyl-6-cyclohexylthio-2-triazine-2,4(1H,3H)-dione |
| 2-allyl-2-thiopseudourea | cyclopropylmethyl isocyanate | " | 3-cyclopropylmethyl-6-allylthio-s-triazine-2,4(1H,3H)-dione |
| 2-(3-methylallyl)-2-thiopseudourea | cyclohexylmethyl isocyanate | methyl chlorothiolformate | 3-cyclohexylmethyl-6-(3-methylallylthio)-s-triazine-2,4(1H,3H)-dione |
| 2-propargyl-2-thiopseudourea | allyl isocyanate | methyl chloroformate | 3-allyl-6-propargylthio-s-triazine-2,4(1H,3H)-dione |
| 2-(3-methylpropargyl)-2-thiopseudourea | 3-methylallyl isocyanate | " | 3-(3-methylallyl)-6-(3-methylpropargylthio)-s-triazine-2,4(1H,3H)-dione |
| 2-benzyl-2-thiopseudourea | propargyl isocyanate | " | 3-propargyl-6-benzylthio-s-triazine-2,4(1H,3H)-dione |
| 2-methylpseudourea | 3-methylpropargyl isocyanate | " | 3-(3-methylpropargyl)-6-methoxy-s-triazine-2,4(1H,3H)-dione |
| 2-hexylpseudourea | benzyl isocyanate | " | 3-benzyl-6-hexyloxy-s-triazine-2,4-(1H,3H)-dione |
| 2-methyl-2-thiopseudourea | p-iodophenyl isocyanate | methyl chlorodithioformate | 3-(p-iodophenyl)-6-methylthio-2-thio-s-triazine-2,4(1H,3H)-dione |
| 2-ethyl-2-thiopseudourea | m-tolyl isocyanate | " | 3-(m-tolyl)-6-(ethylthio)-2-thio-s-triazine-2,4(1H,3H)-dione |
| " | p-butylphenyl isocyanate | " | 3-(p-butylphenyl)-6-ethylthio-2-thio-s-triazine-2,4(1H,3H)-dione |
| " | p-nitrophenyl isocyanate | " | 3-(p-nitrophenyl)-6-ethylthio-2-thio-s-triazine-2,4(1H,3H)-dione |
| " | o-methoxyphenyl isocyanate | methyl chlorothiolformate | 3-(o-methoxyphenyl)-6-ethylthio-s-triazine-2,4(1H,3H)-dione |
| " | m-butoxyphenyl isocyanate | " | 3-(m-butoxyphenyl)-6-ethylthio-s-triazine-2,4(1H,3H)-dione |
| 2-methyl-2-thiopseudourea | p-methylthiophenyl isocyanate | " | 3-(p-methylthiophenyl)-6-methylthio-s-triazine-2,4(1H,3H)-dione |
| " | m-butylthiophenyl isocyanate | " | 3-(m-butylthiophenyl)-6-methylthio-s-triazine-2,4(1H,3H)-dione |
| " | p-cyanophenyl isocyanate | " | 3-(p-cyanophenyl)-6-methylthio-s-triazine-2,4(1H,3H)-dione |
| " | m-trifluoromethylphenyl isocyanate | " | 3-(m-trifluoromethylphenyl)-6-methylthio-s-triazine-2,4(1H,3H)-dione |
| " | 3,5-dichlorophenyl isocyanate | methyl chloroformate | 3-(3,5-dichlorophenyl)-6-methylthio-s-triazine-2,4(1H,3H)-dione |
| " | p-bromo-m-chlorophenyl isocyanate | " | 3-(p-bromo-m-chlorophenyl)-6-methylthio-s-triazine-2,4(1H,3H)-dione |
| " | 2-chloro-4-methylphenyl isocyanate | " | 3-(2-chloro-4-methylphenyl)-6-methylthio-s-triazine-2,4(1H,3H)-dione |
| " | o-fluorophenyl isocyanate | " | 3-(o-fluorophenyl)-6-methylthio-s-triazine-2,4(1H,3H)-dione |
| " | 2-methyl-4-chlorophenyl isocyanate | " | 3-(2-methyl-4-chlorophenyl)-6-methylthio-s-triazine-2,4(1H,3H)-dione |
| " | 2-ethylhexyl isocyanate | " | 3-(2-ethylhexyl)-6-methylthio-s-triazine-2,4(1H,3H)-dione |
| 2-ethylpseudourea | 2-chloro-5-methoxyphenyl isocyanate | " | 3-(2-chloro-5-methoxyphenyl)-6-ethoxy-s-triazine-2,4(1H,3H)-dione |
| " | 3-methyl-4-bromophenyl isocyanate | " | 3-(3-methyl-4-bromophenyl)-6-ethoxy-s-triazine-2,4(1H,3H)-dione |
| " | 2-bromo-4-nitrophenyl isocyanate | " | 3-(2-bromo-4-nitrophenyl)-6-ethoxy-s-triazine-2,4(1H,3H)-dione |
| " | 2-nitro-4-chlorophenyl isocyanate | " | 3-(2-nitro-4-chlorophenyl)-6-ethoxy-s-triazine-2,4(1H,3H)-dione |
| " | 2,4-dichlorophenyl isocyanate | " | 3-(2,4-dichlorophenyl)-6-ethoxy-s-triazine-2,4(1H,3H)-dione |
| 2-methylpseudourea | 2,4-dibromophenyl isocyanate | " | 3-(2,4-dibromophenyl)-6-methoxy-s-triazine-2,4(1H,3H)-dione |
| " | 2,5-dichloro-4-nitrophenyl isocyanate | " | 3-(2,5-dichloro-4-nitrophenyl)-6-methoxy-s-triazine-2,4(1H,3H)-dione |
| " | 3,4-diethoxyphenyl isocyanate | " | 3-(3,4-diethoxyphenyl)-6-methoxy-s-triazine-2,4(1H,3H)-dione |
| " | 2,4-difluorophenyl isocyanate | " | 3-(2,4-difluorophenyl)-6-methoxy-s-triazine-2,4(1H,3H)-dione |
| " | 2,5-dimethoxyphenyl isocyanate | " | 3-(2,5-dimethoxyphenyl)-6-methoxy-s-triazine-2,4(1H,3H)-dione |
| " | 3,5-dinitrophenyl isocyanate | " | 3-(3,5-dinitrophenyl)-6-methoxy-s-triazine-2,4(1H,3H)-dione |
| " | 2-fluoro-4,6-dinitrophenyl isocyanate | " | 3-(2-fluoro-4,6-dinitrophenyl)-6-methoxy-s-triazine-2,4(1H,3H)-dione |
| " | 3-nitro-4-fluorophenyl isocyanate | " | 3-(3-nitro-4-fluorophenyl)-6-methoxy-s-triazine-2,4(1H,3H)-dione |
| " | 2-methyl-4-methoxyphenyl isocyanate | " | 3-(2-methyl-4-methoxyphenyl)-6-methoxy-s-triazine-2,4(1H,3H)-dione |
| " | 2-methoxy-4-nitrophenyl isocyanate | " | 3-(2-methoxy-4-nitrophenyl)-6-methoxy-s-triazine-2,4(1H,3H)-dione |
| " | 2,4,5-trichlorophenyl isocyanate | " | 3-(2,4,5-trichlorophenyl)-6-methoxy-s-triazine-2,4(1H,3H)-dione |
| " | 2,4,6-trimethylphenyl isocyanate | " | 3-(2,4,6-trimethylphenyl)-6-methoxy-s-triazine-2,4(1H,3H)-dione |

EXAMPLE 10

3-Isopropyl-6-methylthio-s-triazine-2,4(1H,3H)-dione

To a solution of 138 parts of 2-methyl-2-thiopseudourea sulfate in 500 parts of water is added 80 parts 50% sodium hydroxide at 0°–10°C. One thousand parts of acetone are added, followed by a dropwise addition of 85 parts of isopropyl isocyanate at 0°C. The reaction mixture is allowed to warm to room temperature in 2 hours. The acetone is evaporated and the solid is filtered and dried to give 150 parts methyl 4-isopropyl-1-thioallophanimidate melting at 81°–85°C.

To a solution of 3.9 parts of phosgene in 100 parts of benzene is added dropwise 8.7 parts of the above compound in 50 parts of tetrahydrofuran. The reaction mixture is heated to reflux, cooled, and 16 parts of 50% sodium hydroxide in 100 parts of water added. After heating the solution to reflux, the benzene layer is discarded and the aqueous layer is neutralized with hydrochloric acid to give after filtration and drying 2 parts of 3-isopropyl-6-methylthio-s-triazine-2,4(1H,3H)-dione melting at 188°–190°C.

EXAMPLE 11

Sodium-3-isopropyl-6-methylthio-s-triazine-2,4-(1H,3H)-dione

To a solution of 1.6 parts of sodium methoxide in 20 parts of methanol is added 6.6 parts of 3-isopropyl-6-methylthio-s-triazine-2,4(1H,3H)-dione. The solution is evaporated under the vacuum and the white solid is triturated with methylene chloride and filtered to give 5.5 parts of sodium 3-isopropyl-6-methylthio-s-triazine-2,4(1H,3H)-dione melting above 300°C.

Similarly, the following s-triazinedione salts can be prepared by using the appropriate starting materials.

| | |
|---|---|
| Lithium | 3-isopropyl-6-methylthio-s-triazine-2,4-(1H,3H)-dione |
| Potassium | 3-isopropyl-6-methylthio-s-triazine-2,4-(1H,3H)-dione |
| Calcium | bis-3-(tert-butyl)-6-methylthio-s-triazine-2,4(1H,3H)-dione |
| Magnesium | bis-3-(tert-butyl)-6-methylthio-s-triazine-2,4(1H,3H)-dione |
| Barium | bis-3-(tert-butyl)-6-methylthio-s-triazine-2,4-(1H,3H)-dione |
| Sodium | 3-(m-trifluoromethylphenyl)-6-methylthio-s-triazine-2,4(1H,3H)-dione |
| Sodium | 3-cyclooctyl-6-methylthio-s-triazine-2,4-(1H,3H)-dione, >300°C. |
| Sodium | 3-(m-fluorophenyl)-6-methylthio-s-triazine-2,4(1H,3H)-dione, >300°C. |
| Sodium | 3-(2-methyl-5-chlorophenyl)-6-methylthio-s-triazine-2,4(1H,3H)-dione, >300°C. |
| Sodium | 3-(3-chloro-4-methylphenyl)-6-methylthio-s-triazine-2,4(1H,3H)-dione, >300°C. |
| Sodium | 3-(2,6-dichlorophenyl)-6-methylthio-s-triazine-2,4(1H,3H)-dione, >300°C. |
| Sodium | 3-(p-tolyl)-6-methylthio-s-triazine-2,4-(1H,3H)-dione, >300°C. |
| Sodium | 3-cycloheptyl-6-methylthio-2-triazine-2,4-(1H,3H)-dione, >300°C. |

EXAMPLE 12

Ammonium 3-(p-chlorophenyl)-6-methoxy-s-triazine-2,4(1H,3H)-dione

To a mixture of 10 parts of 3-(p-chlorophenyl)-6-methoxy-s-triazine-2,4(1H,3H)-dione and 100 parts of methanol is added 1 part of ammonia gas at 20°C. The solution is stirred for 30 minutes and then evaporated under vaccum to give 10.6 parts of ammonium 3-(p-chlorophenyl)-6-methoxy-s-triazine-2,4(1H,3H)-dione.

Similarly, the following s-triazinedione amine salts can be prepared by using the appropriate starting materials.

| | |
|---|---|
| methylammonium | 3-(p-chorophenyl)-6-methoxy-s-triazine-2,4(1H,3H)-dione |
| tri-(2-hydroxyethyl)ammonium | " |
| " | 3-isopropyl-6-ethoxy-s-triazine-2,4-(1H,3H)-dione |
| dimethylammonium | " |
| ethylammonium | " |
| morpholinium | " |
| piperidinium | " |
| butylammonium | 3-(p-chlorophenyl)-6-methylthio-s-triazine-2,4(1H,3H)-dione |
| di-sec-butylammonium | " |
| diethylammonium | " |
| propylammonium | " |
| hexahydroazepidinium | 3-isopropyl-6-methoxy-s-triazine-2,4(1H,3H)-dione |
| pyrrolidinium | " |
| tetraethylammonium | " |
| trimethylammonium | 3-(2-methyl-4-chlorophenyl)-6-methoxy-s-triazine-2,4(1H,3H)-dione |
| tetramethylammonium | " |
| dodecyltrimethylammonium | " |
| 2-hydroxyethylammonium | " |
| benzylammonium | " |
| benzyltrimethylammonium | " |
| triethylammonium | " |

EXAMPLE 13

1-Acetyl-3-isopropyl-6-methylthio-s-triazine-2,4(1H,3H)-dione

To 9.0 parts sodium 3-isopropyl-6-methylthio-s-triazine-2,4(1H,3H)-dione prepared as in Example 10 in 100 parts tetrahydrofuran can be added 3.1 parts acetyl chloride. The reaction can be refluxed for 5 hours and the solvent evaporated. Methylene chloride can be added to the residue and the solution can be washed with 1N sodium hydroxide and brine. After drying and evaporation of the solvent, the residue can be recrystallized from chlorobutane.

Similarly, the following s-triazinediones can be prepared by using appropriate starting materials.

| Starting s-triazinedione | Halide | Product |
|---|---|---|
| 3-isopropyl-6-methylthio-s-triazine-2,4(1H,3H)-dione | butyryl chloride | 1-butyryl-3-isopropyl-6-methylthio-s-triazine-2,4(1H,3H)-dione |
| 3-isopropyl-6-ethoxy-s-triazine-2,4(1H,3H)-dione | methyl chloroformate | 1-methoxycarbonyl-3-isopropyl-6-ethoxy-s-triazine-2,4(1H,3H)-dione |
| 3-(p-chlorophenyl)-6-methoxy-s-triazine-2,4(1H,3H)-dione | methyl chlorothiolformate | 1-methylthiolcarbonyl-3-(p-chlorophenyl)-6-methoxy-s-triazine-2,4(1H,3H)-dione |
| " | n-butyl chloroformate | 1-butylcarbonyl-3-(p-chlorophenyl)-6-methoxy-s-triazin-2,4(1H,3H)-dione |
| 3-(2-methyl-4-chlorophenyl)-6-methylthio-s-triazin-2,4(1H,3H)-dione | n-butyl chlorothiolformate | 1-butylthiolcarbonyl-3-(2-methyl-4-chlorophenyl)-6-methylthio-s-triazine-2,4(1H,3H)-dione |

EXAMPLE 14

3-Isopropyl-6-methoxy-s-triazine-2,4(1H,3H)-dione

A solution of 23 parts of methyl N-(1-amino-1-methoxymethylene)-carbamate, 16 parts of isopropyl isocyanate 60 parts of methylene chloride, and a catalytic amount of dimethylformamide and triethylamine is allowed to stand at room temperature for 3 days. The solvent is evaporated to afford 33 parts of crude methyl 4-isopropyl-N-methoxycarbonylallophanimidate, an oil, $N_D^{25}$ 1.4823.

A solution of 9 parts of the above compound, 10 parts of sodium methoxide, and 100 parts of methanol is refluxed for 1 hr. The solvent is removed under vacuum. Water is then added to the residue. After extraction with methylene chloride, the aqueous layer is neutralized at 5°–10°C. Filtration affords 3 parts of crude solid, which is recrystallized from acetonitrile to give 2 parts of 3-isopropyl-4-methoxy-s-triazine-2,4(1H,3H)-dione, m.p. 195°–200°C.

EXAMPLE 15

3-Isopropyl-6-ethoxy-s-triazine-2,4(1H,3H)-dione

To 114 parts of 2-methylpseudourea sulfate in 400 parts of water at 0°C is added 106 parts of 50% sodium hydroxide, followed by 400 parts of acetone, and 51 parts of isopropyl isocyanate. The reaction mixture is allowed to come to room temperature in 3 hrs. The organic solvent is then evaporated under vacuum, the aqueous residue saturated with sodium chloride, and the mixture extracted with methylene chloride. The organic extract is dried and the methylene chloride evaporated to yield 78 parts of methyl 4-isopropylallophanimidate, m.p. 64°–67°C.

To a solution of 32 parts of the above compound and 24 parts of triethylamine at 0°C is added 27 parts of ethyl chlorothiolformate. The reaction mixture is stirred at room temperature overnight. Water is added and the methylene chloride layer is separated and dried. The methylene chloride is then evaporated to yield 64 parts of crude methyl 4-isopropyl-N-ethylthiolcarbonylallophanimidate, an oil.

A solution of 64 parts of the above compound, 40 parts of sodium methoxide, and 500 parts of ethanol is refluxed for 1 hour. Ethanol is then removed under vacuum and water is added to the residue. After extraction with methylene chloride, the aqueous layer is neutralized at 5°–10°C. with concentrated hydrochloric acid to yield after filtration 8 parts of a solid, which is recrystallized from a mixture of carbontetrachloride/acetonitrile to give 2 parts of 3-isopropyl-6-ethoxy-s-triazine-2,4-(1H,3H)-dione, m.p. 170°–171°C. The methoxy group in the starting material is replaced by an ethoxy group during the reaction in the ethanol solvent.

Formulation and Use of the Compounds

The compounds of this invention are useful herbicides to selectively control weeds in crops such as field corn, sweet corn, rice, asparagus, established nursery stock and certain established fruit trees. The compounds can be applied preemergence, as a directed postemergence treatment or in certain specific cases as an overall postemergence treatment. Application rates range from ½ to 10 kilograms/hectare. Method and rate of application depend upon such factors as crop, soil type, climatic condition and weed population. Uniform distribution of the compounds is important particularly in postemergence treatment.

These compounds may also be combined with other herbicides such as linuron, monuron, diuron, terbacil, and paraquat to control a broader spectrum of weeds.

The compounds of formula I can be formulated in the various ways which are conventional for herbicides of similar physical properties. Useful formulations include wettable and soluble powders, oil suspensions and solutions, aqueous dispersions, dusts, granules, pellets, and high strength compositions. Broadly speaking, these formulations consist essentially of about 1 to 99% by weight of herbicidally active material (including at least one compound of formula I in a herbicidally effective amount) and at least one of a) about 0.1 to 20% by weight of surface active agent and b) about 5 to 99% by weight of essentially biologically inert solid or liquid diluent. More specifically, the various types of formulations will generally contain these ingredients in the following approximate proportions.

|  | Percent By Weight | | |
|---|---|---|---|
|  | Herbicide | Diluent | Surfactant |
| Wettable Powders | 25 – 90 | 0 – 74 | 1 – 10 |
| Oil Suspensions or Solutions | 5 – 35 | 55 – 94 | 1 – 10 |
| Aqueous Dispersions | 10 – 50 | 40 – 89 | 1 – 10 |
| Dusts | 1 – 25 | 70 – 99 | 0 – 5 |
| Granules and Pellets | 1 – 35 | 65 – 99 | 0 – 15 |
| High Strength Compositions | 90 – 99 | 0 – 10 | 0 – 2 |

The actual percentages that can be realized with a particular compound of formula I will depend upon its physical properties.

The manner of making and using such herbicidal formulations is described in numerous patents. See, for example, Luckenbaugh U.S. Pat. No. 3,309,192, Loux U.S. Pat. No. 3,235,357, Todd U.S. Pat. NO. 2,655,445, Hamm et al. U.S. Pat. No. 2,863,752, Scherer et al. U.S. Pat. No. 3,079,244, Gysin et al. U.S. Pat. No. 2,891,855, and Barrous U.S. Pat. No. 2,642,354.

The herbicidal activity of compounds of this invention was discovered in a greenhouse test. In this test, seeds of crabgrass (Digitaria spp.), barnyardgrass (Echinochloa crus-galli), wild oats (Avene fatua), Cassia tora, morningglory (Ipomoea spp.), radish (Raphanus spp.), marigold (Tagetes spp.), dock (Rumex crispus), bean, corn, soybean, rice, wheat and nutsedge tubers were planted in a growth medium and treated preemergence with the chemical dissolved in a nonphytotoxic solvent. At the same time cotton having five leaves (including cotyledonary ones), johnsongrass (Sorghum halepense) having four leaves, crabgrass and barnyardgrass with three leaves and nutsedge (Cyperus rotundus) from tubers with two leaves were treated postemergence. Bush beans with the third trifoliate leaf expanding and sorghum with four leaves were also treated postemergence. Treated plants and controls were maintained in a greenhouse for sixteen days, then all species were compared to controls and visually rated for responses to treatment. A qualitative (type of plant response) rating was made. The letter "C" indicates chlorosis; the letter "B" indicates burn; "G" indicates growth retardation; "D" indicates defoliation; "U" indicates unusual pigmentation; "S" indicates albinism; "I" indicates increased chlorophyll; "EF" indicates early flowering; "DF" indicates delayed flowering; "X" indicates axillary stimulation; "A" indicates growth acceleration; and "Y" indicates increased number of buds or flowers. A qualitative rating on a scale of 0 to 10 was also made; a rating of zero means no effect; a rating of 10 means maximum effect, e.g. complete kill in case of chlorosis. Results obtained in this test for some highly active compounds of this invention are given in the following table; in the table the ampersand symbol stands for the numeral 10.

| Compound | kg per hectare | POST EMERGENCE | | | | | | PRE-EMERGENCE | | | | | | | | | | | | | | |
|---|---|---|---|---|---|---|---|---|---|---|---|---|---|---|---|---|---|---|---|---|---|---|
|  |  | A | B | C | D | E | F | G | H | I | J | K | L | M | N | O | P | Q | R | S | T | U | V | W |
| 3-(m-trifluoromethylphenyl)-6-methylthio-s-triazine-2,4(1H,3H)-dione, sodium salt | 11 | 3C | 7B 7D | 5B | 3B 5G | 7C | — | — | 9C | 9C | 7C | &C | 4C | &C | &C | &C | &C | &C | &C | 5C 8H | 4H | 7C | 6C | 7G |
|  | 11 |  |  |  |  |  |  |  |  |  |  |  |  |  |  |  |  |  |  |  |  |  |  |  |
|  | 2.2 | — | — | — | — | — | &C | 4C | 7C | 7C | 6C | 8C | 1C | &C | &C | &C | &C | &C | &C | 9C | 1C | 1H | 5C | 4G |
| 3-tert-butyl-6-methylthio-s-triazine-2,4(1H,3H)-dione | 11 | 3C | 5C | 6C | 8C | 9C | — | — | &E | 8C | 6G | &C | 3G | &C | &C | &C | &C | &C | &C | 9C | 2G | 9C | 6C | 7C |
|  | 11 | 7G |  |  |  |  |  |  |  |  |  |  |  |  |  |  |  |  |  |  |  |  |  |  |
|  | 2.2 | — | — | — | — | — | &D | 3B | 9G | 5G | 3G | 8C | 0 | &C | &C | &C | &C | &C | &C | 9C | 0 | 5C | 4C | 5C |
| 3-isopropyl-6-methylthio-s-triazine-2,4(1H,3H)-dione | 11 | 5C | &C | &C | &C | &C | — | — | &C | &C | 9C | &C | 8C | &C | &C | &C | &C | &C | &C | 5C | 8C | 7C | 8C |
|  | 2.2 | — | — | — | — | — | &C | 2C | &C | &C | 9C | &C | 0 | &C | &C | &C | &C | &C | &C | 0 | 8C | 7C | &C |
| 3-ethyl-6-methylthio-s-triazine-2,4(1H,3H)-dione | 11 | 0 | &C | 7C | 9C | 9C | — | — | 8C | 9C | 8C | &C | 1C | &C | &C | &C | &C | &C | &C | 9C | 2G | 7C | 6C | 6C |
|  | 2.2 | — | — | — | — | — | &C | 1C | 6G | 0 | 3G | 9C | 0 | &C | &C | &C | &C | &C | &C | 8C | 0 | 6C | 2C | 7C |
| 3-sec-butyl-6-methylthio-s-triazine-2,4(1H,3H)-dione | 11 | 3C | 8C 7D | 7C | 9C | &C | — | — | 8C | &C | 7C | &C | 4C | &C | 9C | &C | &C | &C | &C | 7C | 0 | 7C | 7C | 5C |
|  | 2.2 | — | — | — | — | — | 8C | 3C | 8C | 5G | 4C | &C | 0 | &C | &C | &C | &C | &C | &C | 8C | 0 | 6C | 4C | 6C |
| 3-cyclohexyl-6-methoxy-s-triazine-2,4(1H,3H)-dione | 11 | 6C | &C | 2C | 7C | &C | — | — | 6G | &C | 7G | 9C | 0 | &C | &C | &C | &C | 9C | 9C | 3C | 2S 6G | 4C | 6C |
|  | 11 |  |  |  |  |  |  |  |  |  |  |  |  |  |  |  |  |  |  |  |  |  |  |  |
|  | 2.2 | — | — | — | — | 9C | 8C | 5G | &C | 6G | 9C | 0 | &C | &C | &C | &C | 9C | 7C | 2C | 1C 5G | 4C | 7C |
|  | 2.2 |  |  |  |  |  |  |  |  |  |  |  |  |  |  |  |  |  |  |  |  |  |  |  |
| 3-(2-chlorophenyl)-6-methylthio-s-triazine-2,4(1H,3H)-dione | 11 | 0 | &C | 2U | 4C | 6C | — | — | 9C | &C | 8C | &C | 3C | &C | &C | &C | &C | &C | &C | 4C | 8C | 5C | 6C |
|  | 2.2 | — | — | — | — | &C | 2C | 3C | 9C | 2C | 9C | 1C | &C | &C | &C | &C | &C | &C | 0 | 4C | 3C | 4C |
|  | 1.1 | — | 6C | — | — | — | 9C | — |  |  |  |  |  |  |  |  |  |  |  |  |  |  |  |  |
| 3-isopropyl-6-methylthio-s-triazine-2,4(1H,3H)-dione, sodium salt | 11 | 8C | &C | 9C | &C | &C | — | — | 9C | &C | 8C | 9C | 3C | &C | &C | &C | &C | &C | &C | 9C | 5G | 7C | 6C | 8C |
|  | 2.2 | — | — | — | — | — | &C | 8C | 9C | &C | 7C | 9C | 0 | &C | &C | &C | &C | &C | &C | 8C | 0 | 7C | 3C | 6C |
| 3-isopropyl-6-ethoxy-s-triazine-2,4(1H,3H)-dione | 11 | 7C | &C | &C | &C | &C | — | — | &C | &C | 9C | &C | 4C | &C | &C | &C | &C | &C | &C | 9C | 7C | 9C | 8C | 7C |
|  | 2.2 | — | — | — | — | — | &C | &C | &C | &C | 9C | 9C | 0 | &C | &C | &C | &C | &C | &C | 9C | 1C | 8C | 5C | 7C |
|  | 1.1 | 1C | 8C | 7C | 5C | 8C | — | — |  |  |  |  |  |  |  |  |  |  |  |  |  |  |  |  |
|  | 2.2 | 0 | 7C | 5C | 3C | 6C | — | — |  |  |  |  |  |  |  |  |  |  |  |  |  |  |  |  |
| 3-isopropyl-6-methoxy-s-triazine-2,4(1H,3H)-dione | 11 | 8C | 9C | 9C | &C | &C | — | — | &C | &C | 9C | &C | 1C | &C | &C | &C | &C | &C | &C | 9C | 9C | 7C | 8C | 5C | 8C |
|  | 2.2 | — | — | — | — | — | 9C | 7C | &C | 9C | 7C | &C | 0 | &C | &C | &C | &C | &C | &C | 9C | 7C | 2C | 5C | 4C | 7C |
| 3-isopropyl-6-allylthio-s-trizine-2,4(1H,3H)-dione | 11 | 2C | &C | 8C | &C | &C | — | — | 9C | &C | 5C | &C | 0 | &C | &C | &C | &C | &C | &C | 7C | 1C | 5C | 6C | 7C |
|  | 11 | 9G |  |  |  |  |  |  |  |  |  |  |  |  |  |  |  |  |  |  |  |  |  |  |
|  | 2.2 | — | — | — | — | — | 9C | 7C | &C | &C | 5C | 9C | 0 | &C | &C | &C | &C | &C | &C | 8C | 0 | 3C | 2C | 5C |
|  | 2.2 | 1C | 9C | 5C | 5C | 9C | — | — |  |  |  |  |  |  |  |  |  |  |  |  |  |  |  |  |

-continued

| Compound | kg per hectare | POST EMERGENCE | | | | | | | PRE-EMERGENCE | | | | | | | | | | | | | | |
|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W |
| 3-(2-nitrophenyl)-6-methyl-thio-s-triazine-2,4(1H,3H)-dione | 4.4 | 0 | 5C | 2C | 1C | 4C | — | — | | | | | | | | | | | | | | | |
| | 11 | 0 | 8C | 2C | 8C | 5C | — | — | 9C | &C | &C | &C | 5C | &C | 9C | &C | &C | &C | &C | 8C | &C | 5C | 8C | &C |
| | 2.2 | — | — | — | — | — | &C | 6C | 8C | 5C | 9C | 9C | 0 | 9C | &C | &C | 7C | &C | 8G | 2C | 9C | 3C | 6C | 8C |
| | 2.2 | | | | | | | | | | | | | | | | | | | | 7G | | | |
| | 2.2 | | | | | | | | | | | | | | | | | | | | 7X | | | |
| 3-(4-chlorophenyl)-6-methoxy-s-triazine-2,4(1H,3H)-dione | 11 | 6C | 7C | 0 | 0 | 0 | — | — | 0 | 7C | 4C | 8C | 7C | &C | &C | &C | &C | &C | 9C | 8C | 5G | 5C | 2C | 9C |
| | 11 | EF | | | | | | | | | | | | | | | | | | | | | | |
| | 2.2 | — | — | — | — | — | — | 5G DF Y | 0 | 0 | 5C | 0 | 7C | 0 | &C | &C | &C | 7C | 7C | 6C | 7C | 0 | 1C | 0 | 4C |
| | 2.2 | | | | | | | | | | | | | | | | | | | | | | | | |
| | 2.2 | | | | | | | | | | | | | | | | | | | | | | | | |

A = NUTSEDGE
B = COTTON
C = JOHNSON GRASS
D = CRABGRASS
E = BARNYARD GRASS
F = BEAN
G = SORGHUM
H = CRABGRASS
I = BARNYARD GRASS
J = SORGHUM
K = WILD OATS
L = NUTSEDGE
M = CASSIA
N = MORNING GLORY
O = MUSTARD
P = RADISH
Q = MARIGOLD
R = DOCK
S = BEAN
T = CORN
U = SOYBEAN
V = RICE
W = WHEAT

The capability of preventing pollen formation (gametocidal activity) of 3-(p-chlorophenyl)-6-methoxy-s-triazine-2,4(1H,3H)-dione is shown in the following tests:

A. Foliar sprays of 3-(p-chlorophenyl)-6-methoxy-s-triazine-2,4(1H,3H)-dione on Tenderette bush snap beans in the bud stage prevented fruit set 4 weeks with little effect on vegetative growth. Plants were about 23 days old and 25 to 30 cm tall when sprayed. Plants were passed under a fixed flat-spray nozzle calibrated to deliver 230 liters per hectare. Data from 3 greenhouse tests are summarized below:

| Rate kg/ha | 3 week Response Rating | Average Yield Per Plant at 4 wks | |
|---|---|---|---|
| | | Number of Fruit | Wt. of Fruit (g.) |
| 1.1 | 2G, DF | 0 | 0 |
| .27 | 1X, 1I, DF | 0 | 0 |
| .07 | 0 | 2 | 1.8 |
| 0 | 0 | 16 | 45.9 |

B. Tiny Tim tomatoes with flower buds present were sprayed as above. One plant was treated at each rate and results are indicated below:

| Rate kg/ha | Response Ratings | | Number of Fruit Per Plant | | |
|---|---|---|---|---|---|
| | 19 Days | 47 Days | 19 Days | 47 Days | 73 Days |
| 1.1 | 3C, 2S | 2C, 1A | 0 | 0 | 0 |
| .27 | 2C, 1S | 1C, 2A | 0 | 0 | 1 |
| .07 | 0 | 3A | 0 | 0 | 12 |
| 0 | 0 | 0 | 5 | 21 | 20 |

C. Foliar sprays of corn prior to tasseling have shown control of pollen development and release. Anthers on plants treated at 4, 2 or 1 1lb/A failed to open normally and pollen shed was delayed and reduced.

We claim:

1. The method of controlling weeds in crops comprising applying to the locus of the crop a herbicidally effective amount of a compound of the formula:

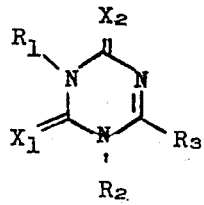

wherein
R₁ is alkyl of 1 through 8 carbon atoms, cycloalkyl of 3 through 8 carbon atoms, cycloalkylalkyl of 4 through 7 carbon atoms, alkenyl of 3 through 4 carbon atoms, alkynyl of 3 through 4 carbon atoms, benzyl, or

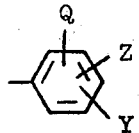

where
Y is hydrogen, halogen, alkyl of 1 through 4 carbon atoms, nitro, alkoxy of 1 through 4 carbon atoms, alkylthio of 1 through 4 carbon atoms, cyano, or trifluoromethyl; and
Z is hydrogen, halogen, methyl, ethyl, nitro, alkoxy of 1 through 4 carbon atoms, or alkylthio of 1 through 4 carbon atoms; and
Q is hydrogen, halogen, or methyl;
$R_2$ is hydrogen, or a group

where A is alkyl of 1 through 3 carbon atoms or alkoxy or alkylthio of 1 through 4 carbon atoms, or a cation selected from lithium, sodium, potassium, calcium, magnesium, barium, or

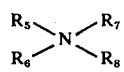

where
$R_5$, $R_6$ and $R_7$ can be the same or different and each can be hydrogen, alkyl of 1 through 4 carbon atoms, or hydroxy alkyl of 2 through 4 carbon atoms; and $R_8$ is hydrogen, alkyl of 1 through 12 carbon atoms, or benzyl; $R_5$ and $R_6$ can be taken together to form a ring that is $-(CH_2)_2-O-(CH_2)_2-$ or $-(CH_2)_n-$ where n is 4–6 and $R_7$ and $R_8$ are H;
$R_3$ is $SR_4$ or $OR_4$ where
$R_4$ is alkyl of 1 through 6 carbon atoms, cycloalkyl of 3 through 6 carbon atoms, alkenyl of 3 through 4 carbon atoms, alkynyl of 3 through 4 carbon atoms, or benzyl, and
$X_1$ and $X_2$ are oxygen or sulfur.

2. The method of claim 1 wherein the crop is corn.

3. A herbicidal composition useful for controlling weeds in crops comprising a herbicidally effective amount of a compound of the formula:

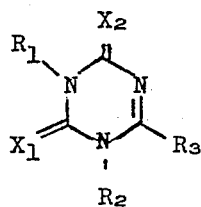

wherein
$R_1$ is alkyl of 1 through 8 carbon atoms, cycloalkyl of 3 through 8 carbon atoms, cycloalkylalkyl of 4 through 7 carbon atoms, alkenyl of 3 through 4 carbon atoms, alkynyl of 3 through 4 carbon atoms, benzyl, or

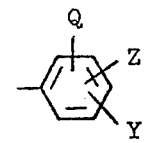

where
Y is hydrogen, halogen, alkyl of 1 through 4 carbon atoms, nitro, alkoxy of 1 through 4 carbon atoms, alkylthio of 1 through 4 carbon atoms, cyano, or trifluoromethyl; and
Z is hydrogen, halogen, methyl, ethyl, nitro, alkoxy of 1 through 4 carbon atoms, or alkylthio of 1 through 4 carbon atoms; and
Q is hydrogen, halogen, or methyl;
$R_2$ is hydrogen, or a group

where A is alkyl of 1 through 3 carbon atoms or alkoxy or alkylthio of 1 through 4 carbon atoms, or a cation selected from lithium, sodium, potassium, calcium, magnesium, barium, or

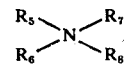

where
$R_5$, $R_6$, and $R_7$ can be the same or different and each can be hydrogen, alkyl of 1 through 4 carbon atoms, or hydroxy alkyl of 2 through 4 carbon atoms; and $R_8$ is hydrogen, alkyl of 1 through 12 carbon atoms, or benzyl; $R_5$ and $R_6$ can be taken together to form a ring that is $-(CH_2)_2-O-(CH_2)_2-$ or $-(CH_2)_n-$ where n is 4–6 and $R_7$ and $R_8$ are H;
$R_3$ is $SR_4$ or $OR_4$ where
$R_4$ is alkyl of 1 through 6 carbon atoms, cycloalkyl of 3 through 6 carbon atoms, alkenyl of 3 through 4 carbon atoms, alkynyl of 3 through 4 carbon atoms, or benzyl, and
$X_1$ and $X_2$ are oxygen or sulfur.
with a herbicidal adjuvant.

* * * * *